US012119093B2

(12) United States Patent
Bardorz et al.

(10) Patent No.: US 12,119,093 B2
(45) Date of Patent: Oct. 15, 2024

(54) EXTRACORPOREAL BLOOD TREATMENT DEVICE AND METHOD FOR OUTPUTTING A REPORT TO AN EXTRACORPOREAL BLOOD TREATMENT DEVICE

(71) Applicant: FRESENIUS MEDICAL CARE DEUTSCHLAND GMBH, Bad Homburg (DE)

(72) Inventors: Christoph Bardorz, Rottendorf (DE); Olaf Nicholas, Kitzingen (DE); Carsten Mueller, Euerbach (DE); Karin Helga Trauner, Schweinfurt (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 901 days.

(21) Appl. No.: 16/347,056

(22) PCT Filed: Nov. 3, 2017

(86) PCT No.: PCT/EP2017/001279
§ 371 (c)(1),
(2) Date: May 2, 2019

(87) PCT Pub. No.: WO2018/082813
PCT Pub. Date: May 11, 2018

(65) Prior Publication Data
US 2020/0075159 A1 Mar. 5, 2020

(30) Foreign Application Priority Data
Nov. 3, 2016 (DE) ...................... 10 2016 013 127.6

(51) Int. Cl.
| | | |
|---|---|---|
| G16H 10/40 | (2018.01) | |
| A61B 5/00 | (2006.01) | |
| A61M 1/14 | (2006.01) | |
| A61M 1/36 | (2006.01) | |
| G16H 40/63 | (2018.01) | |

(52) U.S. Cl.
CPC ............. *G16H 10/40* (2018.01); *G16H 40/63* (2018.01); *A61B 5/7405* (2013.01); *A61B 5/742* (2013.01); *A61M 1/14* (2013.01); *A61M 1/3621* (2013.01)

(58) Field of Classification Search
CPC ...... G16H 10/40; G16H 40/63; A61B 5/7405; A61B 5/742; A61M 1/14; A61M 1/3621
See application file for complete search history.

(56) References Cited

U.S. PATENT DOCUMENTS

| | | | | |
|---|---|---|---|---|
| 2013/0018355 A1* | 1/2013 | Brand | ................... | G16H 40/67 604/93.01 |
| 2013/0228505 A1* | 9/2013 | Burbank | ................... | A61J 1/05 210/257.2 |
| 2013/0310726 A1* | 11/2013 | Miller | ................... | G16H 20/40 717/173 |
| 2015/0025449 A1* | 1/2015 | Yuds | ................... | G16Z 99/00 604/28 |
| 2015/0148697 A1* | 5/2015 | Burnes | ................... | G16H 20/17 600/513 |
| 2016/0151592 A1 | 6/2016 | Sherman et al. | | |

FOREIGN PATENT DOCUMENTS

| | | |
|---|---|---|
| CN | 103262085 A | 8/2013 |
| DE | 102009054415 | 7/2011 |
| DE | 102011108784 | 1/2013 |
| EP | 1838356 | 10/2007 |
| WO | WO 2006/074429 | 7/2006 |

OTHER PUBLICATIONS

John T. Daugirdas and James E. Tattersall, Automated monitoring of hemodialysis adequacy by dialysis machines: potential benefits to patients and cost savings, 78(9) Kidney International p. 833-835 (Nov. 1, 2010) (Year: 2010).*
Thomas Roy, Patients' safety and haemodialysis devices, 16: Editorial Comments Nephrol Dial Transplant 2138-2142 (Year: 2001).*
Fresenius 4008 Hemodialysis System, Technical Manual, Fresenius Medical Care (Apr. 12, 2012) (Year: 2012).*
Prismaflex Machine, Gambro Prismaflex Dialysis—User training (Aug. 6, 2008) (Year: 2008).*
Roy Thomas "Patient's safety and haemodialysis devices", Nephrology Dialysis Transplantation, Bd. 16, Nr. 11, Nov. 1, 2001 (Nov. 1, 1002), Seiten 2138-2142, XP093114129, GB, ISSN: 0931-0509, DOI: 1093/ndt/16.11.2138.
Anonymous: Dialog+ Dialysis Machine—May 31, 2016 XP055643203 B|Braun Sharing Experience.

* cited by examiner

*Primary Examiner* — Jordan L Jackson
(74) *Attorney, Agent, or Firm* — Jacobson Holman PLLC

(57) ABSTRACT

The present invention relates to an extracorporeal blood treatment device comprising at least one output unit for outputting at least one report to a user of the blood treatment device, wherein the blood treatment device is configured to output at least one report by means of the output device after the end of a specific period of time since the switching on of the blood treatment device and/or on the occurrence of a specific event, said report relating to one or more pieces of information relating to the validity of a test carried out at the blood treatment device.

6 Claims, No Drawings

EXTRACORPOREAL BLOOD TREATMENT DEVICE AND METHOD FOR OUTPUTTING A REPORT TO AN EXTRACORPOREAL BLOOD TREATMENT DEVICE

The present invention relates to an extracorporeal blood treatment device having at least one output unit for outputting at least one report to a user of the blood treatment device.

Within the framework of the present invention, an extracorporeal blood treatment device is understood as a device for treating blood that has at least one extracorporeal blood circuit. A treatment of the blood of a patient such as blood purification or the separation of the blood into specific components takes place in the extracorporeal circuit.

In a preferred embodiment of the invention, the blood treatment device is a dialysis machine.

The user of the device within the framework of the present invention is the patient or a person from the staff or another person who is not in the direct vicinity of the device, but rather e.g. in a monitoring center arranged remote from the device.

There is the need with dialysis machines to periodically carry out a so-called T1 test that comprises a functional check of the protective systems of the device. This test is respectively carried out at the restart of the device, triggered either by the user of the device or by the device itself. The test is carried out before every treatment and is always valid for one treatment. The test loses its validity on a treatment time>24 h.

If the device is not switched off after 24 h because a treatment is running and if an interruption is not considered, for instance because it may lead to a threat for the patient, no test of the protective systems takes place after this period of time either. The case can thus occur that no new test has been carried out even though the treatment time exceeds 24 h.

It is the underlying object of the present invention to further develop a blood treatment device of the initially named kind such that the probability for the carrying out of a device test is increased.

This object is achieved by a blood treatment device having the features of aspect 1 below. The extracorporeal blood treatment device is also simply called a "device" in the following.

Provision is accordingly made that the device is configured to output at least one report by means of the output unit that relates to one or more pieces of information relating to the validity of a test carried out at the device after a specific period of time since the switching on of the device, i.e. after a specific operating time and/or on the occurrence of a specific event.

The user of the device is thus advised of the validity of a device test last carried out after the end of a specific operating time of the device and/or on the occurrence of a specific event. The term of the "validity of a test carried out at the device" is to be widely interpreted and comprises not only the communication on how long or whether the test last carried out is still valid, but also, for example, the prompt to carry out a restart of the device or to switch off the device, etc. within a specific period of time.

In accordance with a preferred embodiment of the invention, the device is configured to output at least one first report after a first period of time (e.g. after an operating time of 18 h) from the switching on of the device, i.e. after a first operating time, the first report relating to the current operating time and/or to the permitted operating time or to the difference of the two values and/or having the content that a restart of the device is required within a specific time, with the first period of time being smaller than the permitted operating time, i.e. than the permitted period of time between two tests to be carried out at the blood treatment device.

The permitted period of time between two tests carried out at the device can, for example, amount to 24 h, i.e. a new device test is to be carried out after an operating time of 24 h at the latest.

The aforesaid values and also the values named in the following are examples that do not restrict the invention.

This report can be repeated at specific time intervals, e.g. hourly.

Provision can furthermore be made that the device is configured to output at least one second report after the end of a second period of time from the switching on of the device, i.e. after a second operating time, the second report having the content that the device has to be switched off, with the second period of time being larger than the first period of time. This second report is thus a warning to the user that the device has to be switched off.

If the permitted operating time between two tests is, for example, 24 h, i.e. a new test of the device has to take place after 24 h at the latest, the second period of time can for example, amount to 23 h 45 min or can even be more than 24 h. The second period of time can thus be slightly (e.g. 15 min. to 30 min.) below the permitted period of time between two tests carried out at the device or can exceed it, i.e. can amount to >24 h in the aforesaid example. This second report can also be repeated at specific time intervals, e.g. hourly.

It is furthermore conceivable that the specific event is the transition of the device into the stand-by mode or the end of a treatment carried out by means of the device. The above-named first report and/or the above-named second report can thus be output, for example, when the blood treatment device moves into the stand-by mode and is in the stand-by mode for a specific time period. The same applies accordingly when the treatment has been concluded and a specific operating time, e.g. 18 h or 24 h, has been exceeded.

In a preferred embodiment of the invention, the device is a dialysis machine.

The specific event can also be the exceeding of the planned remaining treatment time (or the exceeding of the remaining ultrafiltration time) beyond a limit value, with the limit value depending on the difference of the operating time of the device up to the second report and of the current operating time or is formed by this difference. That period of time is understood as the remaining ultrafiltration time that is still necessary to draw the prescribed ultrafiltration volume from the blood of the patient in the ongoing treatment. If this remaining ultrafiltration time amounts, for example, to 5 h and if the difference of the operating time of the device up to the second report (e.g. 24 h) and the current operating time (e.g. 22 h) is only 2 h, a report is output in this embodiment, preferably the above-named first report. The first report can be output when there is still a specific period of time up to the second report. It is thus conceivable, for example, that the first report is output after 1 h operating time if the planned remaining treatment time (or the remaining ultrafiltration time) is greater than the difference between the operating time up to the second report and the current operating time and if optionally there is still a specific period of time, e.g. 30 min., up to the second report.

The extracorporeal blood treatment device can have at least one safety unit that is configured to prevent a repeated operation of the blood treatment device if no new test was carried out, i.e. no valid test is present.

It is furthermore conceivable that the second report is carried out in two different variants, wherein the first variant is output when the device is in the mode of extracorporeal blood treatment, and wherein the second variant is output when the device is in any other mode.

The output unit can, for example, be a monitor or display and/or a loudspeaker and/or a transmitter by means of which the at least one report can be transmitted to at least one other unit, preferably by remote data transmission (e.g. internet, mobile radio, etc.).

The named test can, for example, be the T1 test for a dialysis machine, but the invention is not restricted thereto.

The test can be configured such that in particular electrical and/or electronic components or connections are tested, for example a ROM test, a RAM test, a test of excess voltage hardware shutdown, a test of the ADC channels, etc.

The device can have at least one controller that carries out or instigates the above-named steps.

The present invention furthermore relates to a method for generating one or more reports to an extracorporeal blood treatment device in accordance with one of the, wherein the method runs in accordance with the method steps named in the aspects 1 to 9. The method in accordance with the invention can thus comprise one or more of the measures that are named in the aspects 1 to 9 and that are carried out by the extracorporeal blood treatment device.

The aspects 1-10 of the invention are:
1. An extracorporeal blood treatment device comprising at least one output unit for outputting at least one report to a user of the blood treatment device, characterized in that the blood treatment device is configured to output at least one report by means of the output device after the end of a specific period of time since the switching on of the blood treatment device and/or on the occurrence of a specific event, said report relating to one or more pieces of information relating to the validity of a test carried out at the blood treatment device.
2. An extracorporeal blood treatment device in accordance with aspect 1, characterized in that the blood treatment device is configured to output at least one first report after the end of a first period of time, said first report relating to the current operating time and/or to the permitted operating time or their difference and/or having the content that a restart of the blood treatment device is required within a specific time, with the first period of time being smaller than the permitted operating time of the device.
3. An extracorporeal blood treatment device in accordance with aspect 2, characterized in that the blood treatment device is configured to output at least one second report after the end of a second period of time, said second report having the content that the blood treatment device has to be switched off, with the second period of time being greater than the first period of time.
4. An extracorporeal blood treatment device in accordance with aspect 3, characterized in that the second period of time is slightly below the permitted operating time, i.e. the permitted period of time between two tests carried out at the blood treatment device, or exceeds it.
5. An extracorporeal blood treatment device in accordance with one of the aspects 2 to 4, characterized in that the blood treatment device is configured to output the first report again at specific time intervals after the end of the first period of time and/or to output the second report at specific time intervals after the end of the second period of time.
6. An extracorporeal blood treatment device in accordance with one of the preceding aspects, characterized in that the specific event is the transition of the blood treatment device into the stand-by mode or the end of a treatment carried out by means of the blood treatment device.
7. An extracorporeal blood treatment device in accordance with one of the aspects 3 to 6, characterized in that the blood treatment device is a dialysis machine; and in that the specific event is the exceeding of the planned residual treatment time (or exceeding of the residual ultrafiltration time) beyond a limit value, with the limit value depending on the difference between the operating time of the device up to the second report and on the current operating time or being formed by this difference.
8. An extracorporeal blood treatment device in accordance with one of the preceding aspects, characterized in that the blood treatment device has at least one safety device that is configured to prevent a repeat operation of the blood treatment device if no test has been carried out.
9. An extracorporeal blood treatment device in accordance with one of the preceding aspects, characterized in that the output unit is a display and/or a loudspeaker and/or a transmission unit by means of which the at least one report can be transmitted to at least one other unit.
10. A method for outputting one or more reports to an extracorporeal blood treatment device in accordance with one or more of the aspects 1 to 9, wherein the method runs in accordance with one or more of the method steps named in aspects 1 to 9.

The method is thus preferably carried out such that at least one report is output by means of the output unit that relates to one or more pieces of information relating to the validity of a test carried out at the blood treatment device after the end of a specific period of time since the switching on of the blood treatment device and/or on the occurrence of a specific event.

After the end of a first period of time, at least one first report can be output that relates to the current operating time and/or to the permitted operating time or the difference of the two values or has the content that a restart of the blood treatment device is necessary within a specific time, wherein the first period of time is smaller than the permitted period of time between two tests carried out at the blood treatment device.

The method can furthermore be configured such that, after the end of a second period of time, at least one second report is output that has the content that the blood treatment device has to be switched off, with the second period of time being greater than the first period of time. Provision is preferably made in this respect that the second period of time is slightly below or exceeds the permitted period of time between two tests carried out at the blood treatment test.

Provision is made in a further preferred embodiment of the method that, after the end of the first period of time, the first report is output again at specific time intervals and/or, after the end of the second period of time, the second report is again output at specific time intervals.

Provision can furthermore be made that the specific event is the transition of the blood treatment device into the stand-by mode or the end of a treatment carried out by means of the blood treatment device. The first report or the second report preferably only takes place after the end of a specific operating time in these cases.

As stated above, the blood treatment device can be a dialysis machine, wherein the method is configured such that the specific event is the exceeding of the planned remaining treatment time (or the exceeding of the remaining ultrafiltration time) beyond a limit value, with the limit value depending on the difference between the operating time of the device up to the second report and the current operating time or being formed by this difference.

The method can furthermore be configured such that a new operation of the blood treatment device is prevented if no new test was carried out.

The output of the at least one report to a user can take place by means of a monitor or a display and/or a loudspeaker and/or by means of a transmission unit by means of which the at least one report can be transmitted to at least one other unit.

Further details and advantages of the invention will be explained in more detail with reference to the embodiment described in the following:

If the device is switched on by the user or automatically (Auto On program, power failure without battery), the operating time, i.e. the time since the switching on, is measured.

There are the following reports in connection with the operating time:

A first report with the output of the operating time and a prompt to switch off the device after 24 h operating time at the latest.

The first report could be:

"xy hours of operating time have already been reached. The permitted operating time of the device is 24 h. Switch the device off and back on again before the next treatment."

"xy" here stands for the current operating time, i.e. the period of time since the switching on of the device.

In addition, the following first piece of information could be output to the user:

"To allow safety-directed function tests to be carried out automatically and to allow further treatments without interruption, the device must be switched off and back on again after a maximum operating time of 24 h. The operating time is the time period from the switching on to the switching off of the device."

The user can be prompted to acknowledge the reading of this report or piece of information by actuating a button.

The first report and, optionally, the first piece of information is output to the user, for example, after an operating time of 18 h. This applies both during the treatment and if the device is in the stand-by mode.

After an operating time of 18 h, the report can e.g. be repeated hourly until the device is switched off.

The first report and, optionally, the first piece of information is also output on every transition into the stand-by mode or at the end of a treatment when the operating time on the transition into the stand-by mode or at the end of treatment amounts to at least 18 h.

The first report is furthermore already output after 1 h operating time if the remaining UF time is larger than the difference between the operating time for the second report and the current operating time and if the remaining time up to the second report still has a minimum value, e.g. 30 min.

After the end of an operating time of 24 h or briefly before the end of the operating time of 24 h, a second report and, optionally, a second piece of information is output. A repetition subsequently takes place, e.g. hourly, until the device is switched off.

There are two variants for the second report that will be called 2A and 2B in the following.

Report 2A is output when the treatment is ongoing and report 2B is output in all other modes of the device.

The first time, the report 2A is output after 23 h 45 min. in accordance with this embodiment so that the user has sufficient time to end a treatment.

Report 2B also appears on every transition into the stand-by mode or at the end of a treatment if the operating time up to the transition into the stand-by mode or up to the treatment end amounts to at least 24 h.

In the stand-by mode, the first report and the report 2B are only displayed if no auto-off report is visible from which the user can see that the device switches itself off after the end of a specific time in the stand-by mode.

All the reports, i.e. the first report and the reports 2A and 2B, can be acknowledged by the user.

An error memory entry, e.g. in the form of the message "Permitted operating time exceeded (xx h)" takes place at every hourly increment with an operating time>24 h.

The report 2A could be:

"Permitted operating time of the device exceeded. yz hours have already been reached. Stop treatment immediately and start reinfusion! Switch the device off and back on again before the next treatment."

yz here stands for the current operating time of the device, i.e. for the period of time since the last switching on. This applies accordingly to the report 2B named in the following.

The information text optionally output in this respect can correspond to the text named in the first report.

The report 2B could be:

"Permitted operating time of the device exceeded. yz hours have already been reached. Switch device off and back on again."

The information text optionally output in this respect can correspond to the text named in the first report.

The invention claimed is:

1. An extracorporeal dialysis machine performing the steps of:
   (a) outputting at least one report to a user of the dialysis machine, characterized in that the dialysis machine is configured to output the at least one report a specific period of time after switching on of the dialysis machine and/or on the occurrence of a specific event, said report relating to one or more pieces of information relating to the validity of a T1 test carried out at the dialysis machine, and
   (b) preventing a repeat operation of the dialysis machine if no T1 test has been carried out, wherein the dialysis machine is configured to output (i) at least one first report at the end of a first period of time, said first report relating to duration of a current operating time and/or to a permitted maximum continuous operating time, i.e. the permitted period of time between two tests carried out at the dialysis machine, with the first period of time being smaller than the maximum continuous permitted operating time of the device, (ii) the first report again after a fixed time interval after the end of the first period and to prompt the user to confirm reading of the first report, and (iii) at least one second report at specific time intervals after the end of a second period of time greater than the first period of time, the second report having the content that the dialysis machine has to be switched off, with second report output in a first variant if the dialysis machine is currently in a treatment mode and/or the second report output in a second variant if the dialysis machine is in a mode different from a treatment mode.

2. An extracorporeal dialysis machine in accordance with claim 1, characterized in that the second period of time is below the permitted operating time or exceeds the permitted operating time.

3. An extracorporeal dialysis machine in accordance with claim 1, characterized in that the dialysis machine is configured to output the first report again at specific time intervals after the end of the first period of time and/or to output the second report at specific time intervals after the end of the second period of time.

4. An extracorporeal dialysis machine in accordance with claim 1, characterized in that the specific event is the transition of the dialysis machine into a stand-by mode or the end of a treatment carried out by the dialysis machine.

5. An extracorporeal dialysis machine in accordance with claim 1, characterized in that the specific event is the exceeding of a planned residual treatment time (or exceeding of a residual ultrafiltration time) beyond a limit value, with the limit value depending on the difference between an operating time of the device up to a second report and the current operating time or being formed by this difference.

6. A method for operating the extracorporeal dialysis machine in accordance with claim 1, wherein the method comprises the steps of outputting the at least one report after the end of a specific period of time since the switching on of the of the dialysis machine and/or on the occurrence of a specific event, the report relating to one or more pieces of information relating to validity of the T1 test carried out at the dialysis machine and detecting by the safety unit the T1 test was not carried out, followed by—preventing by the safety unit starting of operation of the dialysis machine.

* * * * *